United States Patent
Kulstad (10) Patent No.: US 10,869,778 B1
(45) Date of Patent: Dec. 22, 2020

(54) DEVICES, SYSTEMS, AND METHODS FOR TEMPERATURE MANAGEMENT

(71) Applicant: Advanced Cooling Therapy, Inc., Chicago, IL (US)

(72) Inventor: Erik Kulstad, Chicago, IL (US)

(73) Assignee: ADVANCED COOLING THERAPY, INC., Chicago, IL (US)

(*) Notice: Subject to any disclaimer, the term of this patent is extended or adjusted under 35 U.S.C. 154(b) by 182 days.

(21) Appl. No.: 15/703,629

(22) Filed: Sep. 13, 2017

Related U.S. Application Data (60) Provisional application No. 62/393,764, filed on Sep. 13, 2016.

(51) Int. Cl.
    A61F 7/12 (2006.01)
    A61F 7/00 (2006.01)

(52) U.S. Cl.
    CPC ........ *A61F 7/12* (2013.01); *A61F 2007/0054* (2013.01); *A61F 2007/126* (2013.01)

(58) Field of Classification Search
    CPC .............................. A61F 7/12; A61F 2007/126
    See application file for complete search history.

(56) References Cited

U.S. PATENT DOCUMENTS

| | | | |
|---|---|---|---|
| 9,301,871 B2 | 4/2016 | Kulstad et al. | |
| 9,326,890 B2 | 5/2016 | Kulstad et al. | |
| 9,622,909 B2 | 4/2017 | Kulstad et al. | |
| 2002/0095118 A1* | 7/2002 | Bertoch | A61M 16/0488 604/174 |
| 2004/0167593 A1* | 8/2004 | Keller | A61F 7/12 607/105 |
| 2008/0288033 A1* | 11/2008 | Mason | A61F 7/02 607/96 |
| 2010/0087900 A1* | 4/2010 | Flint | A61B 5/1101 607/104 |
| 2012/0265172 A1 | 10/2012 | Kulstad et al. | |
| 2013/0006336 A1 | 1/2013 | Kulstad et al. | |
| 2014/0155965 A1* | 6/2014 | Kulstad | A61F 7/12 607/105 |
| 2016/0106578 A1 | 4/2016 | Kulstad et al. | |
| 2017/0100280 A1 | 4/2017 | Kulstad et al. | |
| 2017/0100281 A1 | 4/2017 | Kulstad et al. | |

OTHER PUBLICATIONS

Asl, et. al., "Ondansetron and Meperidine Prevent Postoperative Shivering After General Anesthesia," Middle East Journal of Anesthesiology, 21(1), 2011.
Badjatia, et. al., "Novel Esophageal Cooling Device for Therapeutic Normothermia," Abstracts from the 6th International Hypothermia and Temperature Management Symposium, Therapeutic Hypothermia and Temperature Management, vol. 6, No. 3, 2016.

(Continued)

*Primary Examiner* — Kaitlyn E Smith
(74) *Attorney, Agent, or Firm* — Neal, Gerber & Eisenberg LLP; Kevin A. O'Connor (57) ABSTRACT

The present technology relates to systems and methods for managing core body temperature in a subject using, for example, an esophageal heat exchange device. In one aspect, the disclosure provides a method for reducing duration of a hospital stay in a subject undergoing core body temperature management.

10 Claims, 2 Drawing Sheets

(56) References Cited

OTHER PUBLICATIONS

Choi, et. al., "Prevention of Shivering During Therapeutic Temprature Modulation: The Columbia Anti-Shivering Protocol," Neurocritical Care, 14(3), 2010.
Chun, et. al., "A Randomized, Clinical Trial of Frozen Versus Standard Nasogastric Tube Placement," World Journal Surg., 33(9), 2009.
Flint, et. al., Therapeutic Hypothermia after Cardiac Arrest: Performance Characteristics and Safety of Surface Cooling with or without Endovascular Cooling, Neurocritical Care, 7(2), 2007.
Hoque, et. al., "A Comparison of Cooling Methods Used in Therapeutic Hypothermia for Perinatal Asphyxia," Pediatrics, 2010.
Hung, et. al., "A novel method to assist nasogastric tube insertion," Emergency Medicine Journal, 25(1) 2008.
Jarrah, et. al., "Surface Cooling after Cardiac Arrest: Effectiveness, Skin Safety, and Adverse Events in Routine Clinical Practice," Neurocritical Care, 14, 2011.
Jurado, et. al., "Continuous Infusion versus Intermittent Bolus Dosing of Vecuronium in Patients Receiving Therapeutic Hypothermia After Sudden Cardiac Arrest," Pharmacotherapy, 31(12), 2011.
Kirtania, et. al., "Esophageal Guidewire-Assisted Nasogastric Tube Insertion in Anesthetized and Intubated Patients: A Prospective Randomized Controlled Study," Anesthesia Analgesia, 114(2), 2012.
Knapik, et. al., "Comparison of intravascular and conventional hypothermia after cardiac arrest," Kardiologia Polska, 69(11), 2011.
Logan, et. al., "Optimal Management of Shivering During Therapeutic Hypothermia After Cardiac Arrest," Critical Care Nurse, vol. 31, No. 6, Dec. 2011.
May, et. al., "Association of the Bedside Shivering Assessment Scale and derived EMG power during therapeutic hypothermia in survivors of cardiac arrest," Resuscitation 82, 2011.
Merchant, et. al., "Therapeutic hypothermia after cardiac arrest: Unintentional overcooling is common using ice packs and conventional cooling blankets," Critical Care Medicine, 34(12 Suppl)., 2006.
Polderman, "Application of therapeutic hypothermia in the intensive care unit," Intensive Care Medicine, 30(5), 2004.
Presciutti, et. al., "Shivering Management During Therapeutic Temperature Modulation: Nurses' Perspective," Critical Care Nurse, 32(1), 2012.
Scaravilli, et. al., "Fever Management in SAH," Neurocritical Care, 15(2), 2011.
Sessler, "Complications and Treatment of Mild Hypothermia," Anesthesiology, 95(2), 2001.
Taniguchi, et. al., "The Effect of Altering Skin-Surface Cooling Speeds on Vasoconstriction and Shivering Thresholds," Anesthesia Analgesia, vol. 113, No. 3, Sep. 2011.
Topjian, et. al., "Induction and maintenance of therapeutic hypothermia after pediatric cardiac arrest: Efficacy of a surface cooling protocol," Pediatric Critical Care Medicine, vol. 12, No. 3, 2011.
Tsai, et. al., "Tying a Slipknot to an Intubation Stylet. for Facilitating Insertion of a Nasogastric Tube in Liver Transplant Recipients: A Prospective, Randomized Study," Transplant Proceedings, 44(2), 2012.
Usta, et. al., "Dexmedetomidine for the prevention of shivering during spinal anesthesia," Clinics, 66(7), 2011.
Weant, et. al., "Pharmacologic Options for Reducing the Shivering Response to Therapeutic Hypothermia," Pharmacotherapy, 30(8), 2010.

\* cited by examiner

DEVICES, SYSTEMS, AND METHODS FOR TEMPERATURE MANAGEMENT

RELATED APPLICATIONS

The present application claims priority to the U.S. provisional patent application No. 62/393,764 filed on Sep. 13, 2016, the contents of which is incorporated herein by reference.

FIELD OF THE INVENTION

The present technology relates to devices, systems, and methods for managing core body temperature in a subject. In one aspect, the present technology relates to a heat exchange device for managing core body temperature in a subject. In one aspect, the present technology relates to a temperature management system including a heat exchange device for managing core body temperature in a subject. In one aspect, the present technology relates to a method of using a heat exchange device or temperature management system for managing core body temperature in a subject.

BACKGROUND OF THE INVENTION

Active temperature management has been shown to be important for a number of conditions. In particular, adults who remain comatose after resuscitation from cardiac arrest, neonates suffering from hypoxic ischemic encephalopathy, and patients undergoing general surgical procedures longer than one hour in duration all have strong recommendations for temperature modulation. More broadly, active temperature management has been shown to be potentially beneficial for certain subsets of traumatic brain injury, including refractory fever in acutely brain injured patients; spinal cord injury; certain subsets of stroke; acute myocardial infarction; traumatic/hemorrhagic cardiac arrest; surgical operations lasting longer than one hour; hepatic encephalopathy; sepsis/septic shock; and raised intracranial pressure. Indeed, temperature management in an operative setting may improve patient outcome and reduce adverse events.

Temperature management has been attempted by surface cooling and intravascular cooling. However, such methods have been shown to have considerable unwanted side effects, including unwanted shivering. In certain instances, the benefits from cooling may be offset by negative consequences from shivering. In addition, intravascular cooling catheters require the time of a physician for insertion and bear the potential risks of line infection and deep venous thrombosis.

Anti-shivering strategies include both non-pharmacological and pharmacological interventions. Non-pharmacological anti-shivering interventions include skin counter-warming (e.g., local warming of the hands, feet, and/or face). Pharmacological anti-shivering interventions include anesthetics, opiates such as meperidine, buspirone, dexmedetomidine, magnesium sulfate, and/or propofol. The use of sedatives as an anti-shivering intervention may prolong the duration of a hospital stay.

BRIEF SUMMARY OF THE INVENTION

The present technology includes devices, systems, and methods for controlling core body temperature of a subject. In certain embodiments, the devices, systems, and methods of the present technology are used for targeted temperature management. One of the common complications of temperature reduction during conventional targeted temperature management (e.g., using intravascular or surface devices) is shivering. The devices, systems, and methods of the present technology minimize the need to assess a subject undergoing targeted temperature management for shivering and/or minimize the need to provide anti-shivering interventions to such subject. Consequently, the devices, systems, and methods of the present technology serve to (i) reduce the burden on the subject's health care team to monitor the subject during the targeted temperature management procedure, which may last for more than 72 hours; (ii) minimize the exposure of the subject to sedating anti-shivering interventions; and/or (iii) reduce the length of time that the subject spends in a hospital setting.

DETAILED DESCRIPTION OF THE INVENTION

In a first aspect, the present technology provides a method for controlling core body temperature in a subject. The method comprises the steps of providing a heat exchange device having a heat exchange region, placing the heat exchange region of the device in a conduit of the subject, and initiating flow of a heat exchange medium through a fluid path in the heat exchange region to control the subject's core body temperature. The method may also comprise assessing the subject for a shivering response during the temperature management procedure. In certain embodiments, the method comprises assessing the subject for a shivering response no more than once every two hours.

In a second aspect, the present technology provides a method for controlling core body temperature in a subject. The method comprises the steps of providing a heat exchange device having a heat exchange region, placing the heat exchange region of the device in a conduit of the subject, and initiating flow of a heat exchange medium through a fluid path in the heat exchange region to control the subject's core body temperature. The method may also comprise positioning a portion of the heat exchange region that extends outside the conduit to minimize direct contact between an outer surface of the heat exchange region and exposed skin of the subject.

In a third aspect, the present technology provides a method for reducing duration of a hospital stay in a subject undergoing core body temperature management. The method comprises the steps of providing a heat exchange device having a heat exchange region, placing the heat exchange region of the device in a conduit of the subject, and initiating flow of a heat exchange medium through a fluid path in the heat exchange region to control the subject's core body temperature. To limit the anti-shivering interventions performed on the subject, the step of initiating the flow of the heat exchange medium may be performed prior to initiation of any anti-shivering interventions. Subsequently, the subject may be assessed for a shivering response and, if present, may be treated with an anti-shivering intervention at that time.

In a fourth aspect, the present technology provides a temperature management system. The temperature management system comprises a heat exchange device comprising an elongate heat exchange region for insertion into a conduit of a subject. The system comprises a thermally insulating sleeve surrounding at least a part of the elongate heat exchange region. In a particular embodiment, the thermally insulating sleeve surrounds a part of the elongate heat exchange region that extends outside the conduit.

At least one aspect of the present technology includes a heat exchange device. The heat exchange device is operable to be placed in a conduit of a subject. The heat exchange device is operable to transfer heat to or from the subject.

In certain embodiments, the conduit comprises the pharynx, esophagus, and/or stomach of the subject.

In certain embodiments, the heat exchange device comprises a heat exchange region. In certain embodiments, the heat exchange region is an elongate heat exchange region. In certain embodiments, the heat exchange region of the heat exchange device includes a lumen providing a fluid path for flow of a heat exchange medium. In certain embodiments, the lumen is defined by at least one heat exchange tube. In certain embodiments, the heat exchange region of the heat exchange device includes an inflow lumen and an outflow lumen. The inflow and outflow lumens may be in fluid communication with each other. In certain embodiments, the inflow lumen is connected to a heat exchange medium input port. In certain embodiments, the outflow lumen is connected to a heat exchange medium output port. In certain embodiments, a volume of heat exchange medium is delivered to the heat exchange region of the heat exchange device and flows along the fluid path provided by the inflow and outflow lumens.

In certain embodiments, the heat exchange device comprises a heat exchange medium input region. The heat exchange medium input region may serve to provide heat exchange medium to the heat exchange region of the heat exchange device. In certain embodiments, the heat exchange medium input region comprises an input tube for delivering the heat exchange medium from a source to the lumen of the heat exchange region. In certain embodiments, the input tube is connected to the heat exchange medium input port such that a lumen of the input tube is in fluid communication with the inflow lumen of the heat exchange region.

In certain embodiments, the heat exchange device comprises a heat exchange medium output region. The heat exchange medium output region may serve to return spent heat exchange medium from the heat exchange region of the heat exchange device back to the source. In certain embodiments, the heat exchange medium output region comprises an output tube for returning the spent heat exchange medium from the lumen of the heat exchange region to the source. In certain embodiments, the output tube is connected to the heat exchange medium output port such that a lumen of the output tube is in fluid communication with the outflow lumen of the heat exchange region.

Indeed, in certain embodiments, the heat exchange device is a component of a closed loop system that operates to circulate heat exchange medium along the fluid path. In certain embodiments, heat exchange medium is supplied in a closed loop pathway of lumen(s) surrounding a central gastric access lumen.

In certain embodiments, the heat exchange region of the heat exchange device comprises at least two concentrically arranged tubes, such as a heat exchange region inflow tube—defining the inflow lumen—and a heat exchange region outflow tube—defining the outflow lumen. Thus, the heat exchange device may be a multi-lumen heat exchange device having a generally coaxial lumen configuration. In certain embodiments, the heat exchange outflow tube is positioned within the heat exchange inflow tube such that the inflow lumen is the outermost lumen. Alternatively, the tubes and lumens that comprise the heat exchange region of the heat exchange device may be arranged in parallel.

In certain embodiments, the heat exchange device includes one or more central tubes. For example, where the heat exchange device is an esophageal heat exchange device, the central tube may be a tube allowing for gastric access.

In certain embodiments, the heat exchange device is an esophageal heat exchange as described in, for example, U.S. Pat. Nos. 8,231,664; 8,444,684; 8,523,929; 8,696,725; 9,326,890, and 9,301,871 and US Patent Application Publication Nos. 2012/0265172 and 2016/0106578, the contents of which are hereby incorporated by reference in their entireties.

In certain embodiments, the esophageal heat exchange device includes a heat exchange region comprising an inflow lumen connected to a heat exchange medium input port and an outflow lumen connected to a heat exchange medium output port; and a distal end configured for insertion into a nostril or mouth of a subject. Thus, in certain embodiments, the esophageal heat exchange device is orally or nasally inserted into the subject. In certain embodiments, the esophageal heat exchange device allows for gastric decompression. In certain embodiments, the esophageal heat exchange device is capable of receiving a separate gastric tube or gastric probe. In certain embodiments, the esophageal heat exchange device includes a gastric access tube capable of receiving the separate gastric tube or gastric probe. In certain embodiments, the gastric probe is a gastric temperature probe.

In certain embodiments, the esophageal heat exchange device is an esophageal cooling device. In certain embodiments, the esophageal cooling device connects to standard hospital suction to provide gastric decompression. In certain embodiments, the esophageal cooling device includes at least three lumens: two outer lumens to circulate coolant from the proximal end of the device to the distal end and back again to the proximal end; and a central lumen used for gastric decompression. In certain embodiments, the central lumen allows for the removal of gastric contents. In certain embodiments, the central lumen allows for the introduction of nutrients or medication. In certain embodiments, the central lumen is defined by a central tube having one or more distal openings. In certain embodiments, the central tube is capable of being connected to a suction system. For example, in certain embodiments, the proximal end of the central tube is configured using a standard taper fitting for connection to hospital suction devices.

In certain embodiments, a thermally insulating sleeve surrounds at least part of an outer surface of the heat exchange region of the heat exchange device. In certain embodiments, the thermally insulating sleeve surrounds at least part of the outer surface of the heat exchange region that extends outside the subject's conduit. In some such embodiments, the sleeve surrounds at least a portion of the outer surface of the heat exchange region that remains external to the subject. In some such embodiments, the sleeve surrounds at least a portion of the outer surface of the heat exchange region that may contact the subject's exposed skin. In a particular example, a thermally insulting sleeve surrounds at least part of an outer surface of a heat exchange region of an esophageal heat exchange device. In some such embodiments, the sleeve surrounds at least a portion of the outer surface of the heat exchange region that extends outside the pharynx of the subject.

In certain embodiments, the thermally insulating sleeve is integrated with the device. In certain embodiments, the thermally insulating sleeve is a separate component from the device.

In certain embodiments, thermally insulating sleeve is an elongate tubular structure having a wall defining an interior lumen, a first end, and a second end. Preferably, the thermally insulating sleeve is sized larger than the heat exchange region of a heat exchange device. For example, the internal diameter of the thermally insulating sleeve allows the passage of the heat exchange region.

In certain embodiments, the thermally insulating sleeve comprises a material having poor thermal conductivity, such as a plastic. In certain embodiments, the plastic is a thermoplastic, thermoset, or elastomer. In certain embodiments, the sleeve is formed by extrusion. In certain embodiments, the sleeve is formed from polyethylene, polypropylene, polyvinyl chloride, polystyrene, polyamides, polyester, polyurethane, or mixtures, co-polymers, and blends thereof. In certain embodiments, the sleeve is formed from silicone. In certain embodiments, the sleeve is a flexible medical grade silicone tube.

In certain embodiments, the wall of the thermally insulating sleeve is of sufficient thickness to thermally insulate an exterior surface of the wall from the contents of the interior lumen. In certain embodiments, the wall of the thermally insulating sleeve is of sufficient thickness to prevent heat transfer between the exterior surface of the wall and a portion of a heat exchange region of a heat exchange device contained with the interior lumen of the sleeve.

In certain embodiments, the thermally insulating sleeve comprises a highly durable material. In certain embodiments, the thermally insulating sleeve comprises relatively bite resistant material. In certain embodiments, the thermally insulating sleeve comprises a bite block to prevent the subject's teeth from clamping down on the heat exchange region of the heat exchange device. In such embodiments, the bite block is configured to protect the heat exchange device. In certain embodiments, the thermally insulating sleeve comprises a retention collar. In certain embodiments, the thermally insulating sleeve comprises a teeth receiving surface.

At least one aspect of the present technology employs a system to manage temperature in a subject, the system including: a heat exchange device and a source of a heat exchange medium. The heat exchange device is capable of interconnection to the source of the heat exchange medium. For example, the source of the heat exchange medium may be a Medi-Therm III Conductive Hyper/Hypothermia System (Gaymar/Stryker), a Blanketrol II or Blanketrol III Hyper-Hypothermia System (Cincinnati Sub-Zero) or equivalent unit. The source of the heat exchange medium operates to circulate the heat exchange medium through the heat exchange device. In certain embodiments, the source of the heat exchange medium includes a reservoir. In certain embodiments, the reservoir is capable of storing the heat exchange medium.

In certain embodiments, the source of the heat exchange medium supplies temperature-controlled fluid, such as water or saline, through a connector hose to the heat exchange device. An accessory temperature probe may interface between the source and the subject to sense subject temperature, which may be displayed on the source's control panel. In certain embodiments, the source includes a circulating pump, heater, and refrigeration system.

In certain embodiments, the system further comprises at least one adapter hose that interfaces to the source of heat exchange medium on a first end and the heat exchange device on a second end. For example, the adapter hose may connect to the source via a mating brass connector. As another example, the adapter hose may connect to the heat exchange device via a male and female connector.

In certain embodiments, the system further comprises a suction unit. In certain embodiments, the heat exchange device interfaces to a suction unit. For example, where the heat exchange device is an esophageal cooling device, the suction unit may provide gastric decompression.

In certain embodiments, the system further comprises a subject temperature probe. In certain embodiments, the source of the heat exchange medium interfaces with a subject temperature probe. The subject temperature probe can be a component of the heat exchange device or a separate device that is capable of being directly or indirectly coupled to the source. Subject temperature probes are commercially available from, for example, Smiths Medical. Subject temperature probes are available for rectal, oral, vaginal, esophageal, or bladder temperature measurement.

In certain embodiments, the system includes: (a) at least one processor; (b) at least one operator interface configured to provide input to the processor; and (c) at least one memory. The system is configured to: (1) receive an operator generated temperature setting and (2) control the temperature of the heat exchange medium and/or the flow rate of heat exchange medium through the heat exchange device.

In certain embodiments, the system senses patient temperature through a patient temperature probe and compares it to a user-selected target patient temperature, adjusting the temperature and/or flow rate of the heat exchange medium appropriately. For example, a patient temperature probe may convert patient temperature data into electronically readable signals that are transmitted to the source of the heat exchange medium, which then, if necessary, automatically adjusts the temperature and/or flow rate of the heat exchange medium to achieve target patient temperature.

In certain embodiments, the term "subject" includes a mammal in need of therapy for a condition, disease, or disorder or the symptoms associated therewith. The term "subject" includes dogs, cats, pigs, cows, sheep, goats, horses, rats, mice and humans. The term "subject" does not exclude an individual that is normal in all respects.

In certain embodiments, the subject is in need of targeted temperature management. In certain embodiments, the subject is febrile. In some such embodiments, the subject is in an intensive care unit. In certain embodiments, the subject is suffering from or is at risk of suffering an ischemia-reperfusion injury.

In certain embodiments, the subject presents with out-of-hospital cardiac arrest (OHCA). In certain embodiments, the subject presents with in-hospital cardiac arrest (IHCA). In certain embodiments, the subject has been resuscitated following cardiac arrest. In some such embodiments, the subject's core body temperature is maintained between about 33° C. and about 36° C., such as about 33° C., about 34° C., about 35° C., or about 36° C., for at least 12 hours. Alternatively, the subject's core body temperature is maintained between about 33° C. and about 36° C. for at least 24 hours, at least 36 hours, at least 48 hours, at least 60 hours, at least 72 hours, at least 84 hours, or at least 96 hours.

In certain embodiments, the subject has hypoxic ischemic encephalopathy. In some such embodiments, the subject's core body temperature is maintained between about 32° C. and about 34° C., such as about 32° C., about 33° C., or about 34° C., for at least 24 hours. Alternatively, the subject's core body temperature is maintained between about 32° C. and about 34° C. for at least 48 hours, at least 72 hours, or at least 96 hours.

In certain embodiments, the subject has suffered a neurological insult, such as a stroke, spinal cord injury, or traumatic brain injury. In some such embodiments, the subject's core body temperature is maintained at normothermia for at least 24 hours. Alternatively, the subject's core body temperature is maintained at normothermia for at least 48 hours, at least 72 hours, or at least 96 hours.

In certain embodiments, the subject has suffered an acute myocardial infarction. In some such embodiments, the subject's core body temperature is maintained between about 33° C. and about 36° C., such as about 33° C., about 34° C., about 35° C., or about 35° C., for at least 12 hours. Alternatively, the subject's core body temperature is maintained between about 33° C. and about 36° C. for at least 24 hours, at least 36 hours, at least 48 hours, at least 60 hours, at least 72 hours, at least 84 hours, or at least 96 hours.

In certain embodiments, the subject is a burn patient. In some such embodiments, the burn patient is undergoing a surgical procedure. In some such embodiments, the burn patient's core body temperature is maintained at normothermia for the duration of the surgical procedure. In some such embodiments, the burn patient's core body temperature is maintained within a target range for the duration of the surgical procedure.

In certain embodiments, the subject is a patient undergoing a surgical operation. In some such embodiments, the surgical operation is scheduled to last for more than one, two, three, four, five, six, seven, or eight hours. In a particular embodiment, the surgical operation is scheduled to last for at least one hour. In some such embodiments, the subject's core body temperature is maintained at normothermia for the duration of the surgical operation. In some such embodiments, the subject's core body temperature is maintained within a target range for the duration of the surgical operation.

In certain embodiments, the heat exchange device is adapted for placement in a conduit, such as an esophagus, of a subject. In certain embodiments, the conduit comprises the pharynx, esophagus, or stomach. In certain embodiments, the conduit comprises the pharynx and esophagus. In certain embodiments, the conduit comprises the pharynx, esophagus, and stomach.

In embodiments where the heat exchange device is an esophageal heat exchange device, the procedure for initiating targeted temperature management in a subject may include obtaining a measurement of the distance between the subject's lips and the subject's earlobe and then from the earlobe to the tip of the xiphoid process. Such measurement can be used to guide the depth of insertion of the device.

In certain embodiments, a distal portion of the esophageal heat exchange region of an esophageal heat exchange device is inserted through the mouth, past the oropharynx and into the esophagus of the subject. In certain embodiments, the distal portion of the heat exchange region of the device is in positioned within the esophagus while a proximal portion of the heat exchange region of the device extends beyond the oropharynx and into the oral cavity. In certain embodiments, the proximal portion of the heat exchange region of the device extends beyond the oral cavity and resides external to the subject.

In certain embodiments, the portion of the device that remains external to the subject following insertion may be positioned to minimize direct contact between an outer surface of the heat exchange region and exposed skin of the subject. For example, a protective surface may be placed between an external portion of the device and the subject's exposed skin. In a particular example, a protective surface may be placed between an external, proximal portion of the heat exchange region of the device and the subject's exposed skin. In certain embodiments, the protective surface is a towel or sheet. In certain embodiments, the protective surface is a thermally insulating sleeve that surrounds a portion of the device. As another example, the external portion of the device may be secured using a securement device, such as an anchor pad, to prevent contact with the subject's exposed skin.

In certain embodiments, the methods disclosed herein are employed to provide therapeutic temperature management in a subject. In certain embodiments, the methods are employed to maintain normothermia in a subject. In certain embodiments, the methods are employed to induce mild hypothermia in a subject, such as establishing and maintaining a core body temperature between about 33° C. and about 36° C. In certain embodiments, the methods are employed to induce moderate hypothermia in a subject, such as establishing and maintaining a core body temperature between about 28° C. and about 32° C.

In certain embodiments, the methods are employed to establish and maintain a core body temperature of less than about 37° C. in the subject. In certain embodiments, the methods are employed to establish and maintain a core body temperature of less than about 36° C. in the subject. In certain embodiments, the methods are employed to establish and maintain a core body temperature of less than about 35° C. in the subject. In certain embodiments, the methods are employed to establish and maintain a core body temperature of less than about 34° C. in the subject. In certain embodiments, the methods are employed to establish and maintain a core body temperature of less than about 33° C. in the subject. In certain embodiments, the methods are employed to establish and maintain a core body temperature of less than about 32° C. in the subject.

In certain embodiments, the methods are employed to establish and maintain a core body temperature between about 32° C. and about 37° C. in the subject, preferably between about 32° C. and about 36° C. In certain embodiments, the methods are employed to establish and maintain a core body temperature between about 33° C. and about 36° C. in the subject. In certain embodiments, the methods are employed to establish and maintain a core body temperature between about 34° C. and about 36° C. in the subject. In certain embodiments, the methods are employed to establish and maintain a core body temperature between about 35° C. and about 36° C. in the subject. In certain embodiments, the methods are employed to establish and maintain a core body temperature between about 32° C. and about 35° C. in the subject. In certain embodiments, the methods are employed to establish and maintain a core body temperature between about 32° C. and about 34° C. in the subject. In certain embodiments, the methods are employed to establish and maintain a core body temperature between about 32° C. and about 33° C. in the subject.

In certain embodiments, the core body temperature of the subject is managed for at least 12, at least 24, at least 36, at least 48, at least 60, at least 72, at least 84, at least 96, at least 108, or at least 120 hours.

At least one aspect of the present technology employs the step(s) of assessing the subject for a shivering response and, optionally, providing at least one anti-shivering intervention if the subject demonstrates shivering.

In certain embodiments, a health care provider assesses shivering by observing piloerection, tactile confirmation of a vibration in the mandible and neck region, visualization of tremors, and/or measurements with electrical signals of muscle activity, such as electromyography (EMG). In certain embodiments, an assessment scale, such as the Bedside Shivering Assessment Scale (BSAS) is employed to assess shivering. The BSAS is a 4-point scale where a score of zero (0) indicates no shivering; a score of one (1) indicates mild shivering; a score of two (2) indicates moderate shivering; and a score of three (3) indicates severe shivering. In certain embodiments, lack of shivering is confirmed by palpation of the masseter, neck, or chest muscles. In certain embodiments, mild shivering comprises shivering localized to the neck or thorax only. In certain embodiments, moderate shivering involves gross movement of the upper extremities. In certain embodiments, severe shivering involves gross movements of the trunk, upper extremities, and lower extremities.

In certain embodiments, a temperature management system enables a user to assess shivering. For example, EMG electrodes may be placed on the subject to evaluate and record electrical activity produced by skeletal muscles, e.g., pectoralis major.

In certain embodiments, the methods for controlling core body temperature include assessing a subject for a shivering response no more than once every two hours. In some such embodiments, the subject is assessed for a shivering response no more than once every three, once every four, once every five, once every six, once every seven, once every eight, once every nine, once every ten, once every eleven, or once every twelve hours. In some such embodiments, the subject is assessed for a shivering response once every two, once every three, once every four, once every five, once every six, once every seven, once every eight, once every nine, once every ten, once every eleven, or once every twelve hours.

Shivering can occur at hypothermic, normothermic, or even hyperthermic stages due to elevation in the hypothalamic thermoregulatory set-point (fever). Shivering interferes with, and may negate, many of the clinical benefits of temperature control. Moreover, many of the anti-shivering interventions developed in conjunction with intravascular and/or external cooling methods, are associated with prolonged sedation, which may result in prolonged obscuration of the neurological exam and prolonged length of stay in the hospital setting.

Current anti-shivering protocols (e.g., the Columbia Anti-Shivering Protocol), which were designed for intravascular cooling methods or external cooling methods, include a series of interventions prior to the initiation of cooling. These baseline anti-shivering interventions include pharmacological interventions, such as acetaminophen, buspirone, and magnesium sulfate, as well as non-pharmacological interventions, such as skin counter-warming. For any subject demonstrating moderate to severe shivering during intravascular or external cooling, the initial intervention a sedating pharmacological intervention, such as an opiate or dexmedetomidine. If this initial intervention is unsuccessful, the subject may be administered a combination of an opiate and dexmedetomidine. Further interventions to achieve deep sedation include propofol. Finally, neuromuscular blockade with boluses of a paralytic (e.g., cisatracurium, pancuronium, vecuronium) may be used to control shivering.

The goal of the Columbia Anti-Shivering Protocol is for each patient to achieve no to minimal shivering, as defined by BSAS score less than or equal to 1. Under the Protocol, shivering is scored hourly using the BSAS.

The devices, systems, and methods disclosed herein minimize the need to assess a subject undergoing targeted temperature management for shivering and/or minimize the need to provide anti-shivering interventions to such subject.

In certain embodiments for providing targeted temperature management to a subject, the targeted temperature management is initiated without providing any anti-shivering interventions to the subject. In some such embodiments, a heat exchange device is inserted into a conduit of the subject prior to providing any anti-shivering interventions to the subject. In some such embodiments, the subject is brought to a target temperature or within a target temperature range prior to providing any anti-shivering interventions.

In certain embodiments, the methods described herein exclude providing anti-shivering interventions prior to initiation of the targeted temperature management procedure (i.e., at baseline). In certain embodiments, the methods described herein exclude providing anti-shivering interventions at any time prior to or during the targeted temperature management procedure.

In certain embodiments, the methods described herein exclude administering pharmacological anti-shivering interventions prior to initiation of the targeted temperature management procedure (i.e., at baseline). In certain embodiments, the methods described herein exclude administering pharmacological anti-shivering interventions at any time prior to or during the targeted temperature management procedure.

In certain embodiments, the methods described herein exclude administering sedating pharmacological anti-shivering interventions prior to initiation of the targeted temperature management procedure (i.e., at baseline). In certain embodiments, the methods described herein exclude administering sedating pharmacological anti-shivering interventions at any time prior to or during the targeted temperature management procedure.

In certain embodiments for providing targeted temperature management to a subject, the subject is assessed for a shivering response and at least one anti-shivering intervention is provided if the subject demonstrates mild shivering. In some such embodiments, the subject is assessed by observation and/or palpation of the masseter, neck, or chest muscles. In certain embodiments for providing targeted temperature management to a subject, at least one anti-shivering intervention is provided if the subject demonstrates shivering localized to the neck or thorax. In certain embodiments, the anti-shivering intervention provided to the subject is a non-pharmacological intervention, such as skin counter-warming. In certain embodiments, the anti-shivering intervention provided to the subject is a non-sedating pharmacological intervention.

In certain embodiments for providing targeted temperature management to a subject, the subject is assessed for a shivering response and at least one anti-shivering intervention is provided if the subject demonstrates moderate shivering. In certain embodiments for providing targeted temperature management to a subject, at least one anti-shivering intervention is provided if the subject demonstrates shivering involving gross movement of the upper extremities. In certain embodiments, the anti-shivering intervention provided to the subject is a non-pharmacological intervention, such as skin counter-warming. In certain embodiments, the anti-shivering intervention provided to the subject is a non-sedating pharmacological intervention.

In certain embodiments for providing targeted temperature management to a subject, the subject is assessed for a shivering response and at least one anti-shivering intervention is provided if the subject demonstrates severe shivering. In certain embodiments for providing targeted temperature management to a subject, at least one anti-shivering intervention is provided if the subject demonstrates shivering involving gross movements of the trunk, upper extremities, and lower extremities. In certain embodiments, the anti-shivering intervention provided to the subject is a non-pharmacological intervention, such as skin counter-warming. In certain embodiments, the anti-shivering intervention provided to the subject is a non-sedating pharmacological intervention.

The present technology involves providing targeted temperature management to a subject. In certain embodiments, a subject receiving targeted temperature management using the present devices or systems or according to the present methods will have a reduced length of stay in a hospital setting relative to a subject—or a population of subjects—receiving conventional targeted temperature management (e.g., using intravascular or surface devices). In certain embodiments, a subject receiving targeted temperature management using the present devices or systems or according to the present methods will have a reduced length of stay in a hospital setting relative to a subject—or a population of subjects—suffering from the same underlying condition but not receiving targeted temperature management.

Certain example embodiments of the presently described technology now will be described with respect to the appended figures; however, the scope of the present technology is not intended to be limited thereby. It is to be understood that the scope of the present technology is not to be limited to the specific embodiments described herein. The technology may be practiced other than as particularly described and still be within the scope of the claims.

Figure 1:
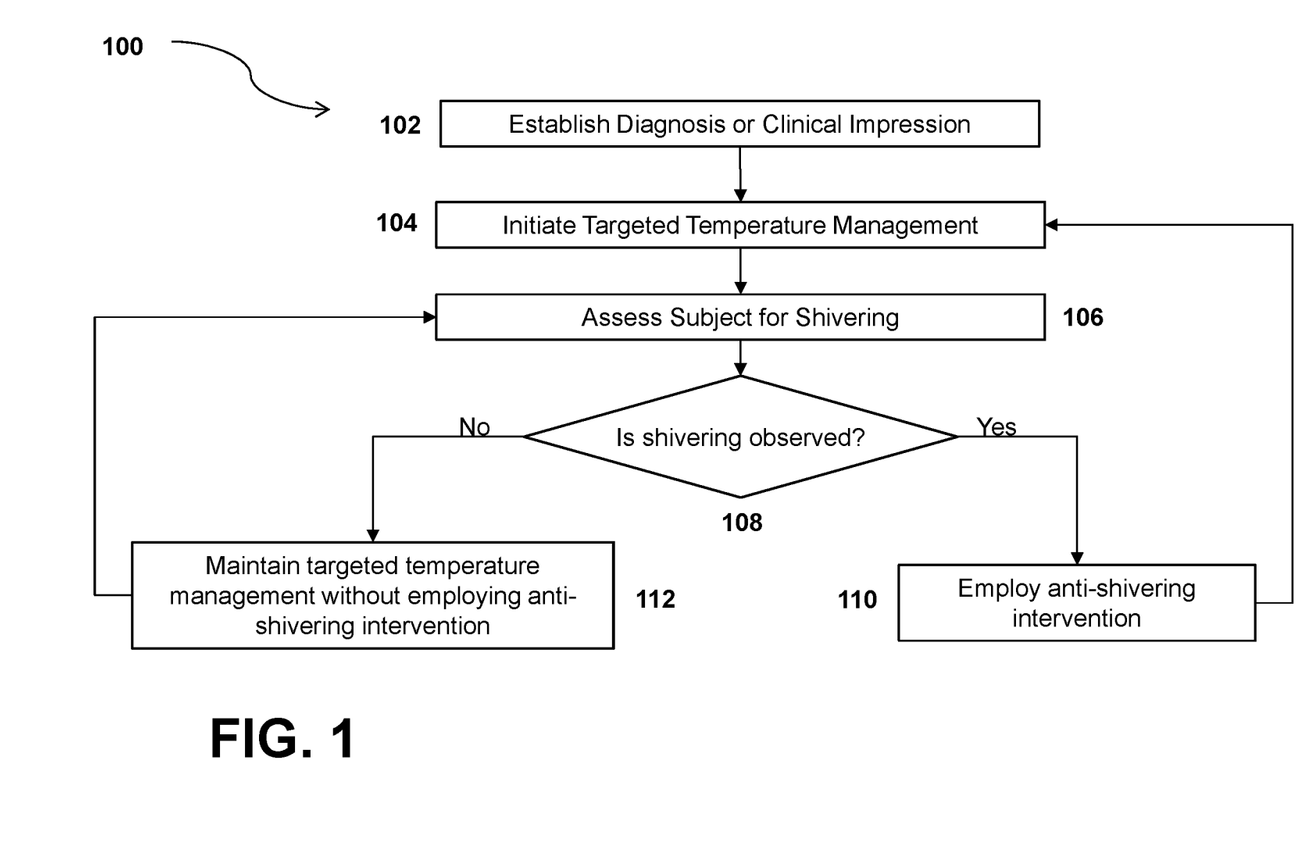
FIG. 1 shows a flowchart according to an exemplary embodiment of the present technology.

FIG. 1 shows a flow diagram of a method 100 for the use of targeted temperature management while avoiding the negative consequences of shivering. According to various embodiments, at least a portion of the activity described with respect to FIG. 1 may be implemented via one or more heat exchange devices described herein.

As shown at 102, an initial diagnosis or clinical impression is established. Such diagnosis or clinical impression may include identifying a subject as a candidate for targeted temperature management. Such diagnosis or clinical impression may be reached on the basis of a physical examination, a patient history, and/or one or more laboratory tests.

After it has been determined that the subject is a candidate for targeted temperature management, targeted temperature management is initiated, as indicated by block 104. In certain embodiments, a temperature management system enables a user to initiate targeted temperature management. In certain embodiments, the method excludes employing pharmacological anti-shivering interventions prior to initiation of targeted temperature management. In certain embodiments, the method excludes administration of any anti-shivering drugs prior to initiation of targeted temperature management.

Following initiation of targeted temperature management, the subject is assessed for shivering, as indicated by block 106. In certain embodiments, a health care provider assesses shivering by observing the subject for signs of shivering, including piloerection or tremors. Such observation may be by direct visualization or via a temperature management system, such as by EMG. In certain embodiments, an assessment scale, such as the BSAS is employed to assess shivering.

As indicated by decision diamond 108, alternative responses occur depending upon whether shivering is observed. If the subject is shivering, an anti-shivering intervention is employed, as indicated in block 110. In certain embodiments, the anti-shivering intervention comprises a non-pharmacological intervention. In certain embodiments, the anti-shivering intervention comprises skin counter-warming. In certain embodiments, the anti-shivering intervention comprises administration of a non-sedating anti-shivering drug. In certain embodiments, the anti-shivering intervention excludes administration of a sedating anti-shivering drug. If no shivering is observed, targeted temperature management is maintained without employing an anti-shivering intervention, as indicated by block 112, and the subject is re-assessed at a later time. In certain embodiments, the later time is at least 1 hour, at least 2 hours, at least 3 hours, at least 4 hours, at least 5 hours, at least 6 hours, at least 7 hours, or at least 8 hours following the previous assessment. In certain embodiments, the later time is about 1 hour, about 2 hours, about 3 hours, about 4 hours, about 5 hours, about 6 hours, about 7 hours, or about 8 hours following the previous assessment.

Figure 2:
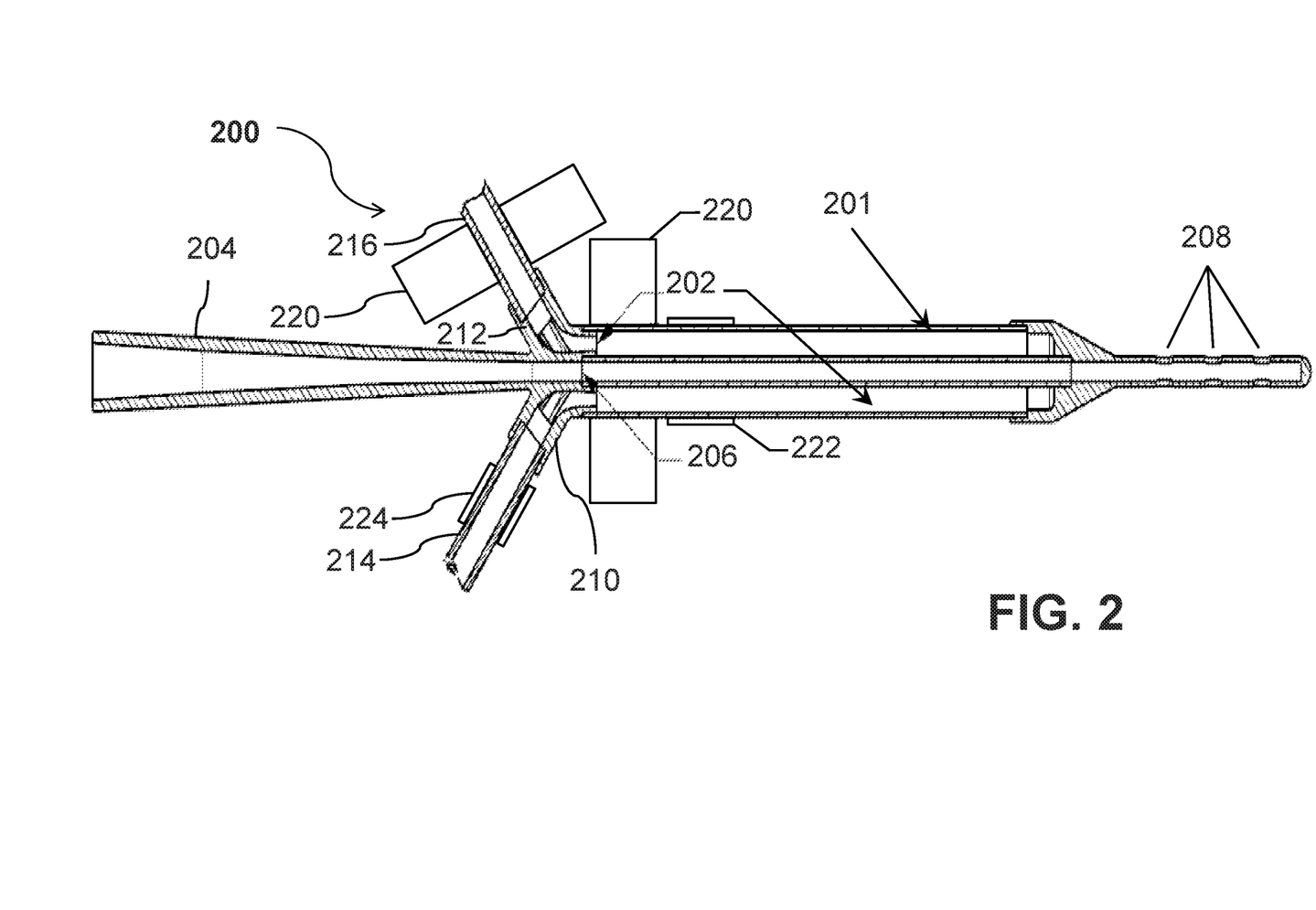
FIG. 2 shows a cross-sectional view of a heat exchange device according to an exemplary embodiment of the present technology.

FIG. 2 is a cross-sectional view of an exemplary heat exchange device 200. The heat exchange device 200 comprises a heat exchange tube 201 defining a lumen 202 and a gastric access tube 204. The gastric access tube 204 defines a gastric access lumen 206. The distal section of the heat exchange device 200 includes one or more ports 208 along the side of the gastric tube 204. The one or more ports 208 may provide for communication between the space exterior to the device 200 and the gastric access lumen 206. For example, the one or more ports 208 may act as a portal between the patient's stomach and the gastric access lumen 206 allowing the gastric contents to be suctioned from the patient's stomach out through the gastric access lumen 206. The presence of multiple ports 208 provides reduced likelihood of blockage of the gastric access lumen 206 from semi-solid stomach contents. Alternatively, multiple gastric access lumens may be employed. The addition of one or more ports 208 may improve and enhance the removal of stomach contents, which, in turn, may improve contact between gastric mucosa and the heat exchange device 200. Such improved contact may enhance heat exchange between the heat exchange device 200 and the gastric mucosa. The configuration of the ports 208 shown in FIG. 2 is oval. However, the ports 208 can be, for example, circular, rectangular, or any other shape that permits flow of gastric contents from the stomach to the gastric access lumen 206.

The heat exchange device 200 includes an input port 210 and an output port 212. Input port 210 may be connected to an input tube 214. Input tube 214 may, for example, carry heat exchange medium from an external source (not shown) to input port 210. Output port 212 may be connected to an output tube 216. Output tube 216 may, for example, carry spent heat exchange medium from device 200 to an external source (not shown).

EXEMPLARY EMBODIMENTS

In one aspect, this disclosure provides a method for controlling core body temperature in a subject in need thereof, the method comprising the steps of providing a heat exchange device, the heat exchange device comprising a heat exchange region having at least one lumen providing a fluid path for flow of a heat exchange medium; placing the heat exchange region of the heat exchange device in a conduit of the subject; initiating flow of the heat exchange medium through the fluid path to achieve or maintain normothermia or hypothermia; and assessing the subject for a shivering response no more than once every two hours. In certain embodiments, the conduit comprises the pharynx, esophagus, or stomach. In certain embodiments, the method further comprises providing at least one anti-shivering intervention if the subject demonstrates mild to severe shivering. In certain embodiments, the method further comprises positioning a portion of the heat exchange region that extends outside the conduit to minimize direct contact between an outer surface of the heat exchange region and exposed skin of the subject. In some such embodiments, the positioning step comprises securing the portion of the heat exchange region that extends outside the conduit with a securement device. In some such embodiments, the securement device is an anchor pad, such as one of the anchor pads 220 of FIG. 2. In certain embodiments, the device further comprises a heat exchange medium input region in fluid communication with the heat exchange region, wherein the input region comprises an input tube for delivering the heat exchange medium from a source to the lumen of the heat exchange region. In certain embodiments, the method further comprises providing a thermally insulating sleeve, such as the thermally insulating sleeve 222 of FIG. 2, surrounding at least part of an outer surface of the heat exchange region that extends outside the conduit.

In another aspect, this disclosure provides a method for controlling core body temperature in a subject in need thereof, the method comprising the steps of providing a heat exchange device, the heat exchange device comprising a heat exchange region having at least one lumen providing a fluid path for flow of a heat exchange medium; placing the heat exchange region of the heat exchange device in a conduit of the subject; positioning a portion of the heat exchange region that extends outside the conduit to minimize direct contact between an outer surface of the heat exchange region and exposed skin of the subject; and initiating flow of the heat exchange medium through the fluid path. In certain embodiments, the conduit comprises the pharynx, esophagus, or stomach. In certain embodiments, the positioning step comprises securing the portion of the heat exchange region that extends outside the conduit with a securement device. In some such embodiments, the securement device is an anchor pad, such as one of the anchor pads 220 of FIG. 2. In certain embodiments, the method further comprises assessing the subject for a shivering response. In certain embodiments, the method further comprises providing at least one anti-shivering intervention if the subject demonstrates mild to severe shivering. In certain embodiments, the device further comprises a heat exchange medium input region in fluid communication with the heat exchange region, wherein the input region comprises an input tube for delivering the heat exchange medium from a source to the lumen of the heat exchange region. In certain embodiments, the method further comprises providing a thermally insulating sleeve, such as the thermally insulating sleeve 222 of FIG. 2, surrounding at least part of an outer surface of the heat exchange region that extends outside the conduit.

In still another aspect, this disclosure provides method for reducing duration of a hospital stay in a subject undergoing core body temperature management, the method comprising the steps of providing a heat exchange device, the heat exchange device comprising a heat exchange region having at least one lumen providing a fluid path for flow of a heat exchange medium; placing the heat exchange region of the heat exchange device in a conduit of the subject; initiating flow of the heat exchange medium through the fluid path to control core body temperature of the subject prior to initiation of any anti-shivering interventions; assessing the subject for a shivering response; and providing at least one anti-shivering intervention if the subject demonstrates mild to severe shivering. In certain embodiments, the conduit comprises the pharynx, esophagus, or stomach. In certain embodiments, the method further comprises positioning a portion of the heat exchange region that extends outside the conduit to minimize direct contact between an outer surface of the heat exchange region and exposed skin of the subject. In some such embodiments, the positioning step comprises securing the portion of the heat exchange region that extends outside the conduit with a securement device. In some such embodiments, the securement device is an anchor pad, such as one of the anchor pads 220 of FIG. 2. In certain embodiments, the anti-shivering intervention provided if the subject demonstrates mild to severe shivering is a non-sedating intervention. In some such embodiments, the non-sedating intervention comprises administering an anti-shivering agent selected from the group consisting of acetaminophen, buspirone, magnesium sulfate, nephopam, meperidine, and combinations thereof or skin counter-warming. In certain embodiments, the method further comprises providing a thermally insulating sleeve, such as the thermally insulating sleeve 222 of FIG. 2 surrounding at least part of an outer surface of the heat exchange region that extends outside the conduit.

In yet another aspect, this disclosure provides temperature management system comprising a heat exchange device comprising an elongate heat exchange region, the elongate heat exchange region comprising at least one tube defining a lumen, wherein the lumen provides a fluid path for flow of a heat exchange medium; and a thermally insulating sleeve, such as the thermally insulating sleeve 222 of FIG. 2, surrounding at least part of an outer surface of said tube. In certain embodiments, the sleeve is integrated with the device. In certain embodiments, the sleeve is a separate component from the device. In certain embodiments, the sleeve is comprised of relatively bite resistant material. In certain embodiments, the sleeve comprises a retention collar. In certain embodiments, the sleeve comprises a teeth receiving surface. In certain embodiments, the temperature management system further comprises a heat exchange medium input region in fluid communication with the heat exchange region, wherein the input region comprises an input tube for delivering the heat exchange medium from a source to the lumen of the heat exchange region. In certain embodiments, the temperature management system further comprises a thermally insulating sleeve, such as the second thermally insulating sleeve 224 of FIG. 2, surrounding at least part of an outer surface of the input tube.

In the preceding paragraphs, temperature is expressed in degrees Celsius. It should be understood that temperature may be expressed in a different manner, such as degrees Fahrenheit or Kelvin.

In the preceding paragraphs, use of the singular includes the plural except where specifically indicated. As used herein, the words "a," "an," and "the" mean "one or more," unless otherwise specified. In addition, where aspects of the present technology are described with reference to lists of alternatives, the technology includes any individual member or subgroup of the list of alternatives and any combinations of one or more thereof.

The disclosures of all patents and publications, including published patent applications, are hereby incorporated by reference in their entireties to the same extent as if each patent and publication were specifically and individually incorporated by reference.

It is to be understood that the scope of the present technology is not to be limited to the specific embodiments described above. The present technology may be practiced other than as particularly described and still be within the scope of the accompanying claims.

The presently described technology is now described in such full, clear, concise and exact terms as to enable any person skilled in the art to which it pertains, to practice the same. The foregoing description of the present technology provides illustration and description, but is not intended to be exhaustive or to limit the technology to the precise one disclosed. Modifications and variations are possible in light of the above teachings or may be acquired from practice of the technology. Thus, it is noted that the scope of the invention is defined by the claims and their equivalents. Therefore, it is to be understood that the foregoing describes preferred embodiments of the technology and that modifications may be made therein without departing from the spirit or scope of the invention as set forth in the appended claims and their equivalents.

What is claimed is:

1. A method for controlling core body temperature in a subject in need thereof, the method comprising the steps of:
   providing a heat exchange device, the heat exchange device comprising a heat exchange region having at least one lumen providing a fluid path for flow of a heat exchange medium;
   orally placing at least a portion of the heat exchange region of the heat exchange device in an esophagus of the subject, wherein a proximal portion of the heat exchange region extends beyond an oral cavity of the subject, wherein a thermally insulating sleeve surrounds at least part of an outer surface of the proximal portion of the heat exchange region extending beyond the oral cavity of the subject, wherein the thermally insulating sleeve comprises an elongate tubular structure;
   positioning the thermally insulating sleeve between the proximal portion of the heat exchange region and exposed skin of the subject to reduce or prevent direct contact between the outer surface of the proximal portion of the heat exchange region and the exposed skin of the subject; and
   initiating flow of the heat exchange medium through the fluid path.

2. The method of claim 1, wherein the positioning step comprises securing the proximal portion of the heat exchange region with a securement device.

3. The method of claim 2, wherein the securement device is an anchor pad.

4. The method of claim 1, further comprising assessing the subject for a shivering response.

5. The method of claim 1, further comprising providing at least one anti-shivering intervention if the subject demonstrates mild to severe shivering.

6. The method of claim 1, wherein the device further comprises a heat exchange medium input region in fluid communication with the heat exchange region, wherein the input region comprises an input tube for delivering the heat exchange medium from a source to the lumen of the heat exchange region.

7. A method for reducing duration of a hospital stay in a subject undergoing core body temperature management, the method comprising the steps of:
   providing a heat exchange device, the heat exchange device comprising a heat exchange region having at least one lumen providing a fluid path for flow of a heat exchange medium;
   orally placing the heat exchange region of the heat exchange device in an esophagus of the subject;
   positioning a proximal portion of the heat exchange region that extends beyond an oral cavity of the subject to reduce or prevent direct contact between an outer surface of the proximal portion of the heat exchange region and exposed skin of the subject, wherein a thermally insulating sleeve comprises an elongate tubular structure that surrounds at least part of an outer surface of the proximal portion of the heat exchange region extending beyond the oral cavity of the subject;
   initiating flow of the heat exchange medium through the fluid path to control core body temperature of the subject prior to initiation of any anti-shivering interventions;
   assessing the subject for a shivering response; and
   providing at least one anti-shivering intervention if and only if the subject demonstrates mild to severe shivering.

8. The method of claim 7, wherein the positioning step comprises securing the proximal portion of the heat exchange region with a securement device.

9. The method of claim 8, wherein the securement device is an anchor pad.

10. The method of claim 7, wherein the anti-shivering intervention is a non-sedating anti-shivering intervention, the non-sedating anti-shivering intervention comprising (i) administering an anti-shivering agent selected from the group consisting of acetaminophen, buspirone, magnesium sulfate, nephopam, meperidine, and combinations thereof or (ii) skin counter-warming.

* * * * *